United States Patent
Tran

(10) Patent No.: US 10,073,998 B1
(45) Date of Patent: Sep. 11, 2018

(54) MULTIFUNCTION WEARABLE OBJECT IDENTIFIED GLASSES FOR THE VISUALLY HANDICAPPED

(71) Applicant: The United States of America as Represented by the Secretary of the Navy, Washington, DC (US)

(72) Inventor: Nghia X. Tran, San Diego, CA (US)

(73) Assignee: The United States of America as representd by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/825,837

(22) Filed: Nov. 29, 2017

(51) Int. Cl.
| | |
|---|---|
| G06K 7/10 | (2006.01) |
| H02J 50/10 | (2016.01) |
| G06K 19/077 | (2006.01) |
| A61F 9/08 | (2006.01) |
| A61F 9/04 | (2006.01) |

(52) U.S. Cl.
CPC ... *G06K 7/10396* (2013.01); *G06K 19/07758* (2013.01); *H02J 50/10* (2016.02); *A61F 9/04* (2013.01); *A61F 9/08* (2013.01)

(58) Field of Classification Search
None
See application file for complete search history.

(56) References Cited

U.S. PATENT DOCUMENTS

| | | | |
|---|---|---|---|
| 5,971,279 A | 10/1999 | Raistrick et al. | |
| 6,877,658 B2 | 4/2005 | Raistrick et al. | |
| 8,279,091 B1 | 10/2012 | Tran et al. | |
| 8,660,491 B1 * | 2/2014 | Tran | H04B 5/0037 455/41.1 |
| 2011/0143321 A1 | 6/2011 | Tran et al. | |
| 2012/0183941 A1 * | 7/2012 | Steinmetz | G06F 19/3462 434/262 |
| 2016/0071390 A1 * | 3/2016 | Sales | A61B 5/1114 340/573.1 |

(Continued)

OTHER PUBLICATIONS

En-Vision America, Inc., ScripTalk Station Pharmacy Quick User Guide.

(Continued)

*Primary Examiner* — Carlos E Garcia
(74) *Attorney, Agent, or Firm* — SPAWAR Systems Center Pacific; Kyle Eppele; Young Fei

(57) ABSTRACT

A radio frequency identification (RFID) label and an RFID data retrieval device which may be used to aid the visually impaired identify the medicines they take. RFID label includes a memory chip, energy harvesting circuit, and a loop antenna, with the memory chip containing information about the medicine. RFID data retrieval device contains a device controller chip, a wireless transceiver, a switch, a loop antenna, a memory chip, a proximity sensor, an audio digital-to-analog converter (DAC), an audio amplifier, an audio speaker, and also a pair of opposing temporal side members connected to a device controller chip retaining member via hinge. This device controller retaining member contains a recessed for the nose of the visually impaired person. The invention may also include an inductive charging device made up of an inductive charge coil, a power converter, a regulator, a charge controller, and an external power supply, allowing for wireless charging.

12 Claims, 14 Drawing Sheets

(56) References Cited

U.S. PATENT DOCUMENTS

2016/0165037 A1\* 6/2016 Youn .................... H04W 8/005
 455/557

OTHER PUBLICATIONS

En-Vision America, Inc., ScripTalk Station User's Guide.
En-Vision America, Inc., ScripAbility Accessible Rx Labels.
Gunnar O. Klein et al, Smart Glasses—A New Tool in Medicine, MEDINFO 2015: eHealth-enabled Health, 2015, 901-01, vol. 216, IMIA and IOS Press.

\* cited by examiner

… (1)

MULTIFUNCTION WEARABLE OBJECT IDENTIFIED GLASSES FOR THE VISUALLY HANDICAPPED

FEDERALLY SPONSORED RESEARCH AND DEVELOPMENT

The Multifunctional Wearable Object Identified Glasses for the Visually Handicapped is assigned to the United States Government and is available for licensing and for commercial purposes. Licensing and technical inquiries may be directed to the Office of Research and Technical Applications, Space and Naval Warfare Systems Center Pacific (Code 72120), San Diego, Calif., 92152 via telephone at (619) 553-2778 or email at ssc_pac_t2@navy.mil. Reference Navy Case Number 103995.

BACKGROUND OF THE INVENTION

There are several methods by which the visually impaired learn and distinguish between the medicines they take. They may identify pills by their shapes, sizes, textures, or smells. They may mark medicine bottles by physically emphasizing letters on medicine bottle caps, or adding Braille labels or tying rubber bands to the bottles themselves. However, as more and more medicines are added to the person's prescription portfolio, the task of distinguishing between medicines becomes increasingly difficult. Integrating a system of electronics onto eyeglasses and medicine bottles aims to provide a convenient way to help the visually impaired (such as the blind or elderly) identify and distinguish between medicines, as well as provide a convenient way of providing instructions to the person using the medicine.

SUMMARY OF THE INVENTION

The present invention is for a system made up of a radio frequency identification (RFID) label and an RFID data retrieval device which may be used to aid the visually impaired identify the medicines they take. The RFID label includes a memory chip, energy harvesting circuit, and a loop antenna, with the memory chip containing information about the medicine. The RFID data retrieval device contains a device controller chip, a wireless transceiver, a switch, a loop antenna, a memory chip, a proximity sensor, an audio digital-to-analog converter (DAC), an audio amplifier, and an audio speaker. The RFID data retrieval device also has a pair of opposing temporal side members connected to a device controller chip retaining member via hinge. This device controller retaining member contains a recessed for the nose of the visually impaired person.

Alternatively, the present invention may also include an inductive charging device made up of an inductive charge coil, a power converter, a regulator, a charge controller, and an external power supply, thus allowing the RFID data retrieval device to be charged wirelessly.

BRIEF DESCRIPTION OF THE DRAWINGS

Throughout the several views, like elements are referenced using like references. The elements in the figures are not drawn to scale, and some dimensions may be exaggerated for clarity.

DETAILED DESCRIPTION OF THE INVENTION

While the invention may be embodied in different forms, the drawings and this section describe in detail specific embodiments of the invention with the understanding that the present disclosure is to be considered merely a preferred embodiment of the invention, and is not intended to limit the invention in any way.

Figure 1:
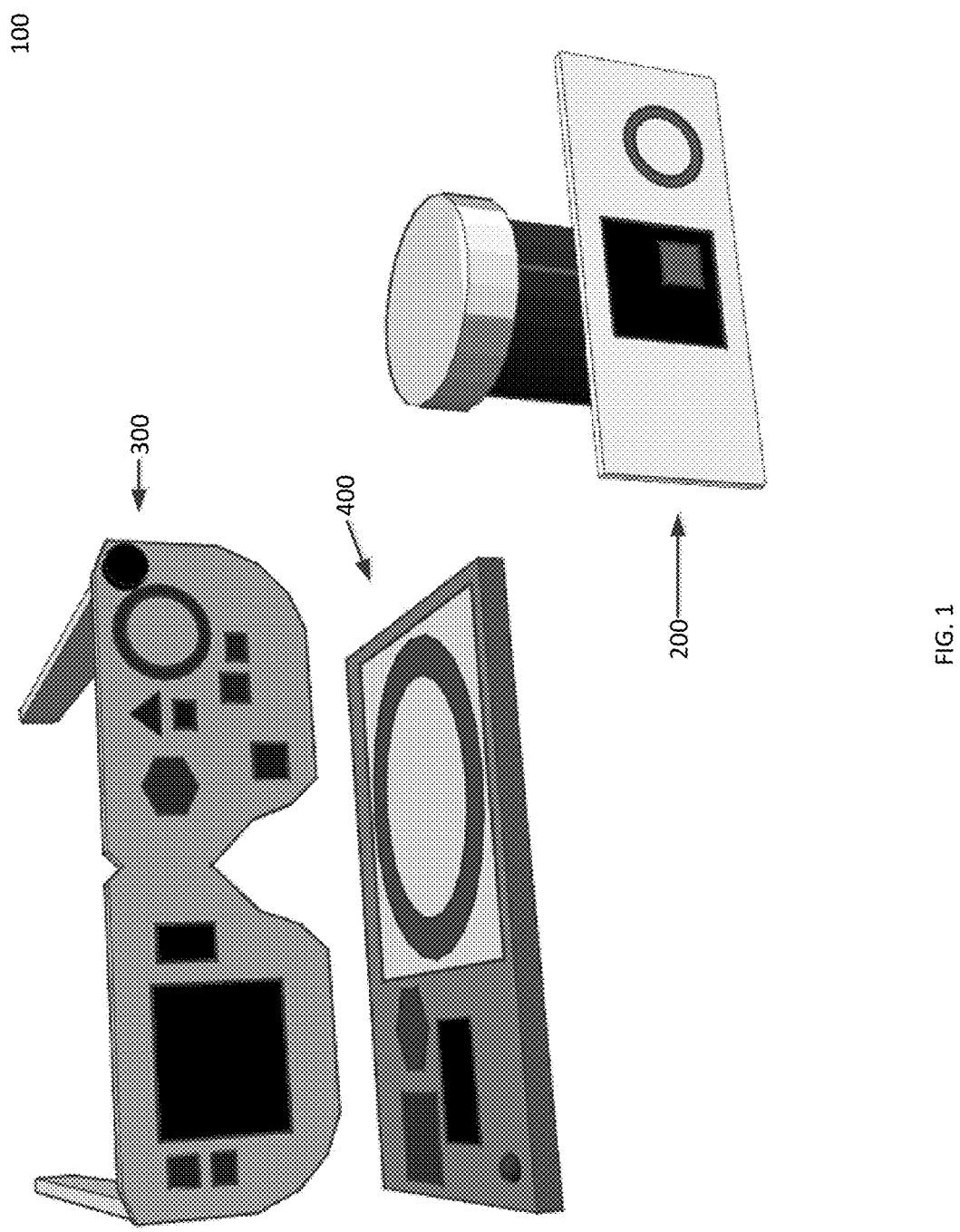
FIG. 1 shows a perspective view of components of a system of Multifunctional Wearable Object Identified Glasses for the Visually Impaired.
Figure 2:
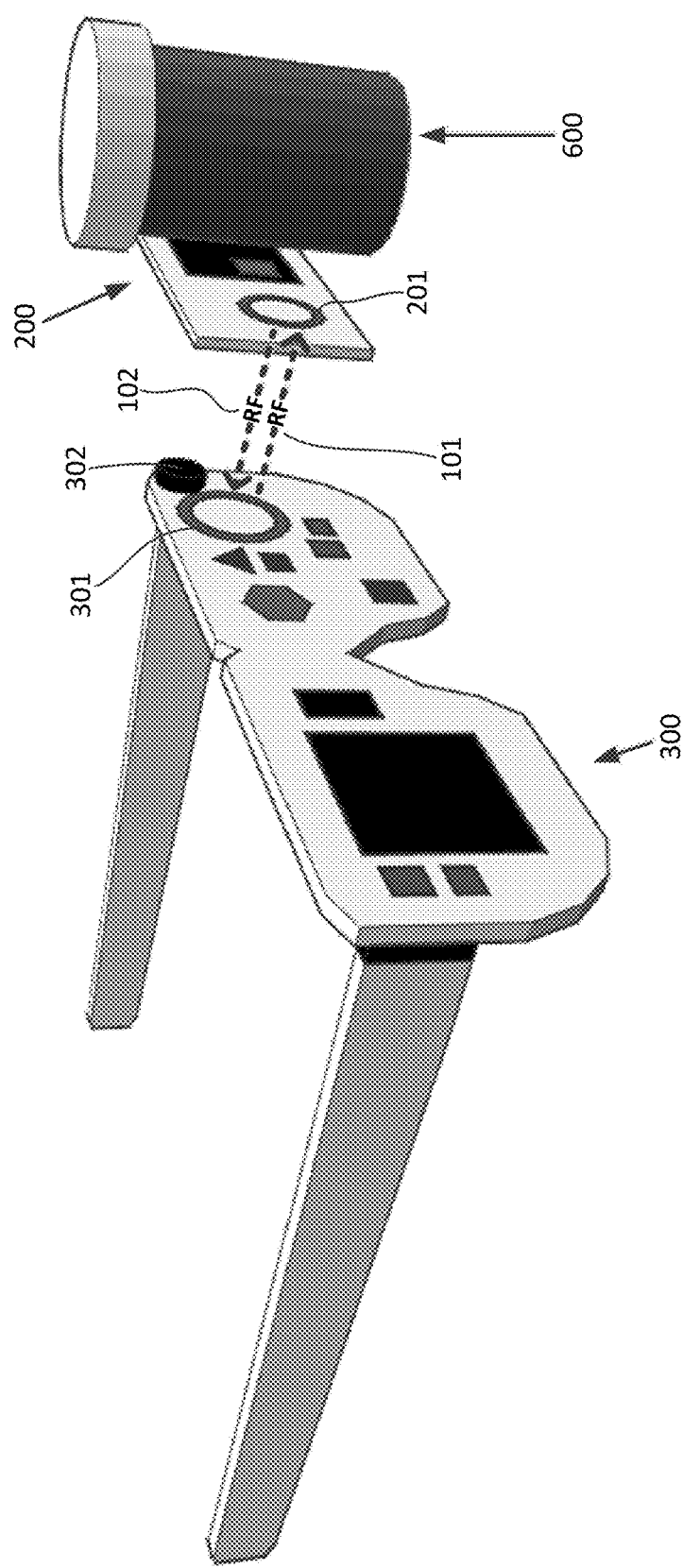
FIG. 2 shows the interaction between an RFID data retrieval device with an RFID label according to the present invention.
Figure 3:
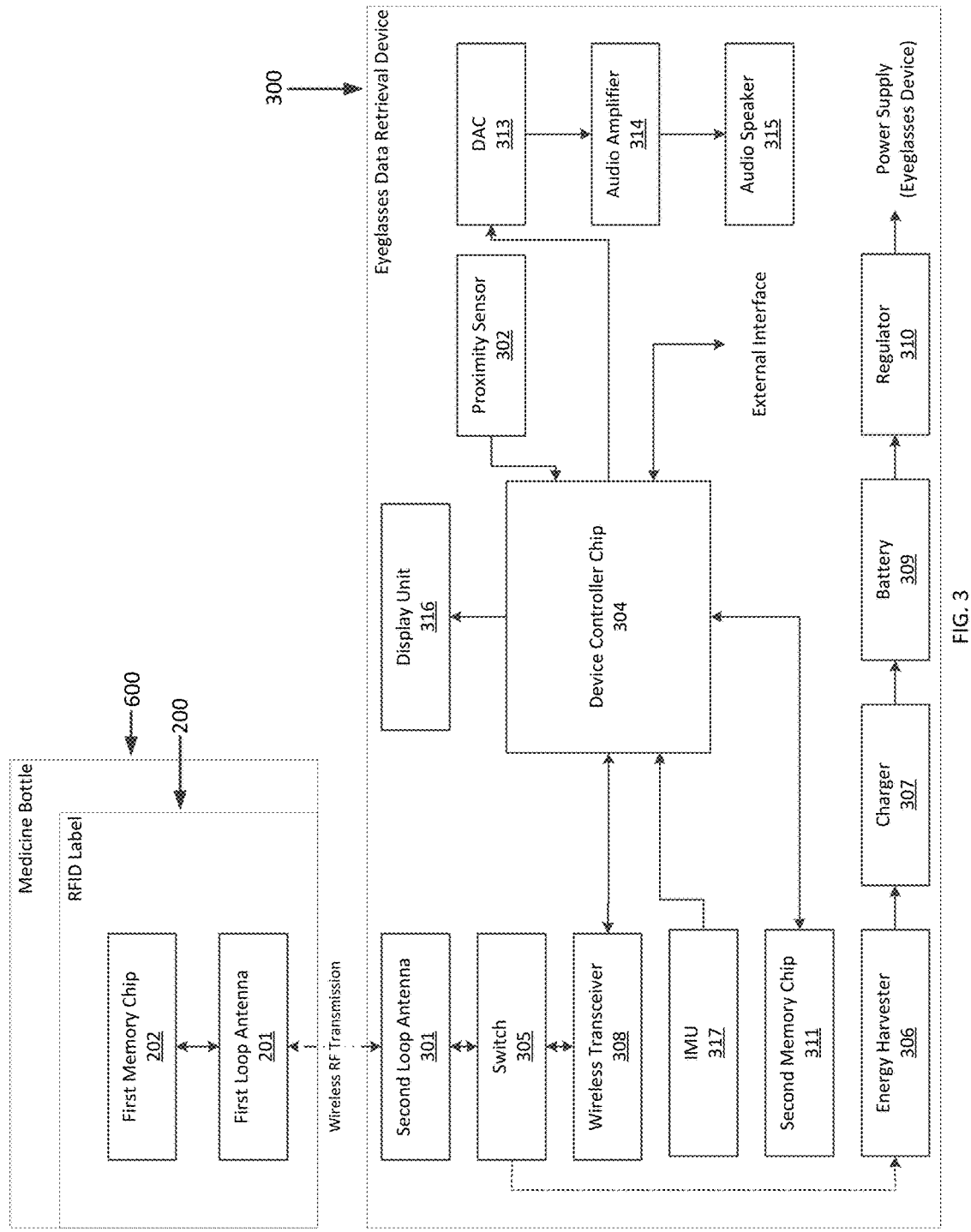
FIG. 3 shows a diagram of an embodiment of a system including an RFID data retrieval device and an RFID label with a wireless-only memory chip according to the present invention.

FIG. 1 depicts an embodiment of the invention, a system 100 with three major components. This embodiment includes an RFID label 200, an RFID data retrieval device 300 in the shape of eyeglasses to be worn by the visually impaired person using the system, and an inductive charging device 400 for wirelessly recharging the data retrieval device 300. FIG. 2 shows the basic function of identifying medication using the system. When a user wants to know the information about the medication contained in medicine bottle 600 (to which RFID data label 200 is attached), the user simply brings medicine bottle 600 and RFID data label 200 near the eyeglasses data retrieval device 300. When the user does so, the proximity sensor 302 will detect the presence of the RFID label 200, transmit a radio frequency (RF) signal 101 via the second loop antenna 301. This RF signal 101 will be received by the first loop antenna 201, and the RF label 200 will transmit the information about the medicine through first loop antenna 201 to second loop antenna 301 via return RF signal 102. The eyeglasses data retrieval system 300 will then be able to tell the user the medicine name and instructions for its use through audio. FIG. 3 shows a block diagram of the configuration of RFID label 200 and eyeglasses data retrieval system 300 in detail.

Figure 4:
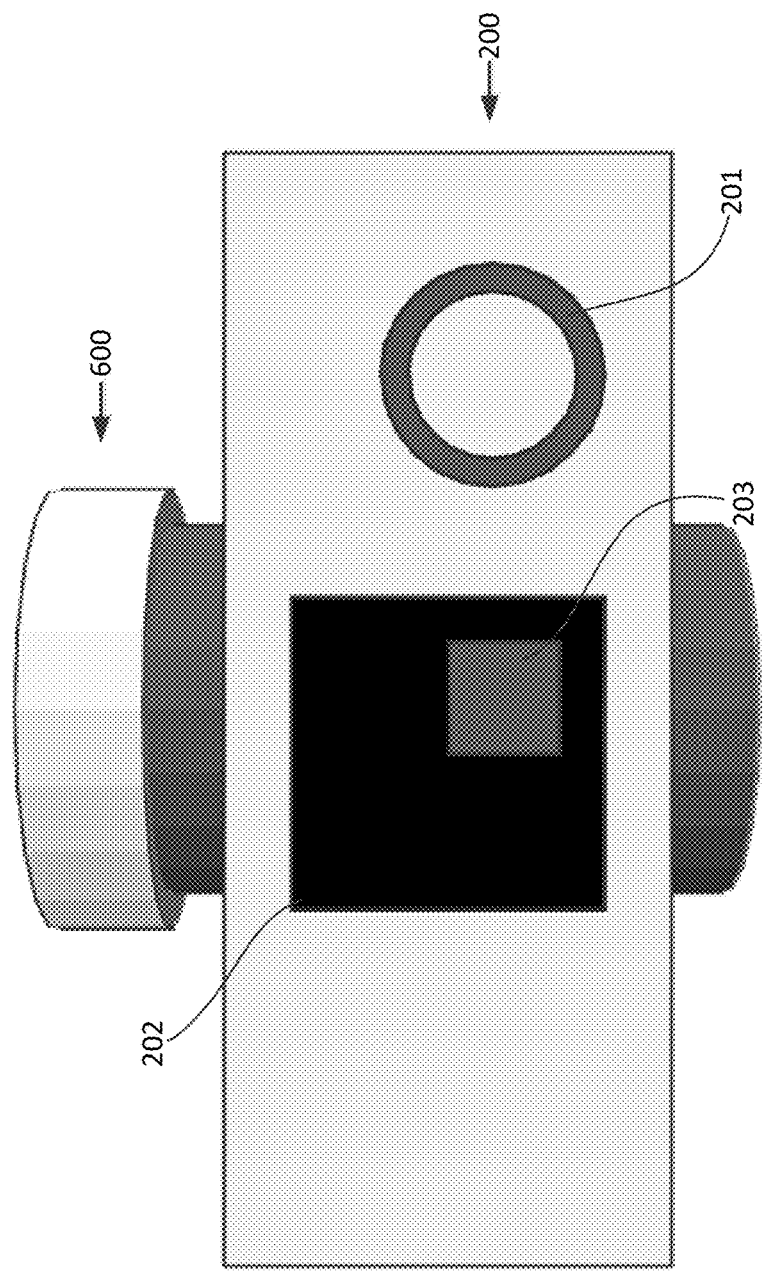
FIG. 4 shows a frontal elevation view of an RFID label with a wireless-only memory chip according to the present invention.

FIG. 4 shows an embodiment of the RFID label 200 in greater detail. In this embodiment, RFID label 200 is affixed to a medicine bottle 600. This embodiment uses a wireless-only first memory chip 202. This wireless first memory chip is comprised of digital logic, memory, and communications circuits which can transmit and receive RF signals. The RFID label 200 or first memory chip 202 also needs to have an internal energy harvesting circuit 203 capable of harvesting energy from an external radio source to power the device. There is no separate battery on this embodiment of the RFID label 200. The RFID label 200 sends and receives RF signals through a first loop antenna 201. Two specific examples of first memory chip 202 that are sufficient for the purposes of this invention include STMicroelectronics' M24LR04E-R and NXP Semiconductors' NT3H1101. These chips can store up to one kilobyte of data, and data contained on these first memory chips 202 can be accessed wirelessly. The data can be configured to be rewritable or nonrewritable depending on the specific application. For example, pharmacy staff may write or rewrite medicine names and usage instructions to the memory, but then configure the memory to be nonrewritable before delivery to patients. After that point, the patient or user can only read the data, but not write, ensuring the integrity of the medical information stored in first memory chip 202.

Figure 5:
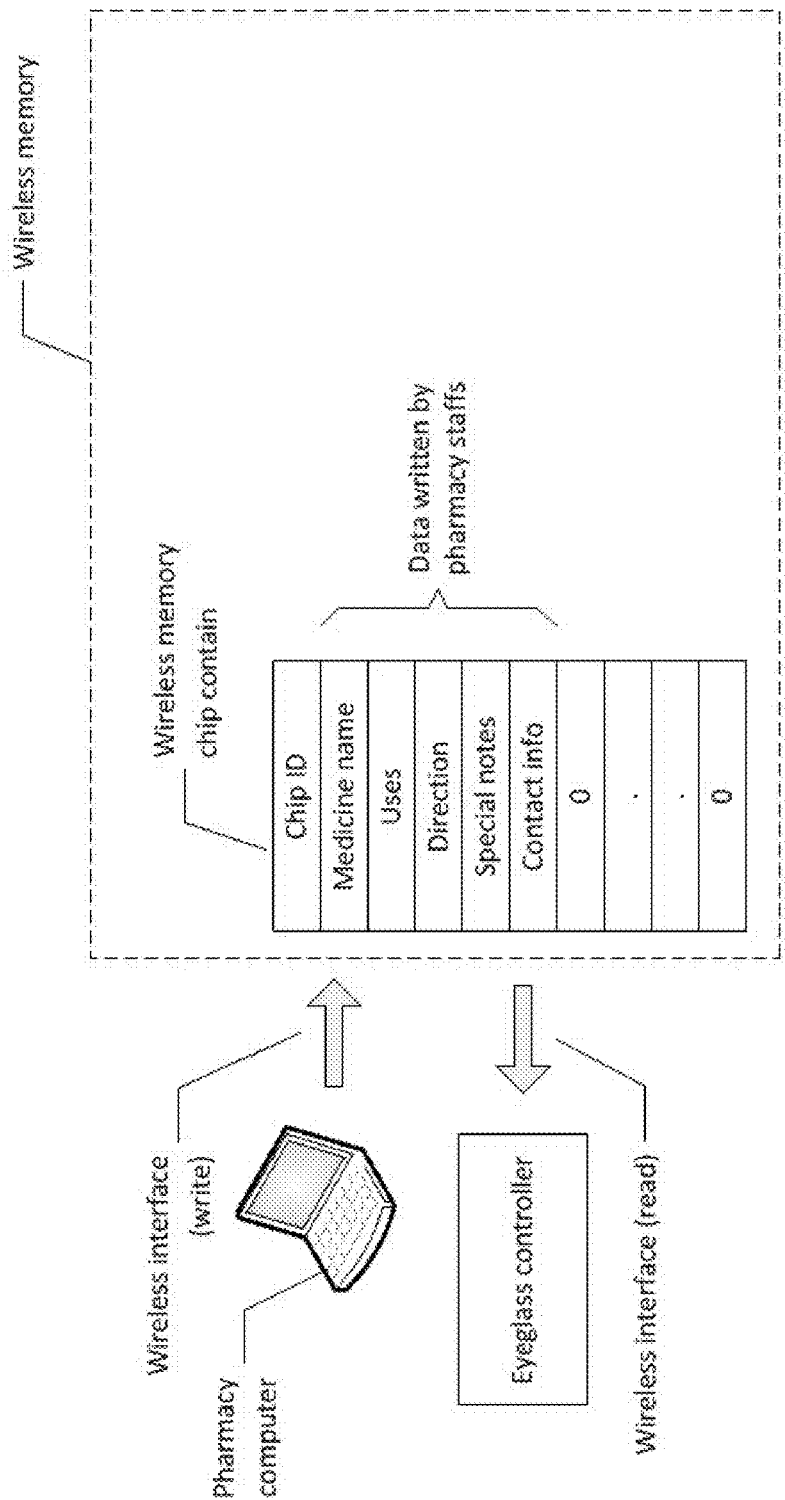
FIG. 5 shows a diagram depicting read and write from and to a wireless-only memory chip on an RFID label according to the present invention.
Figure 6:
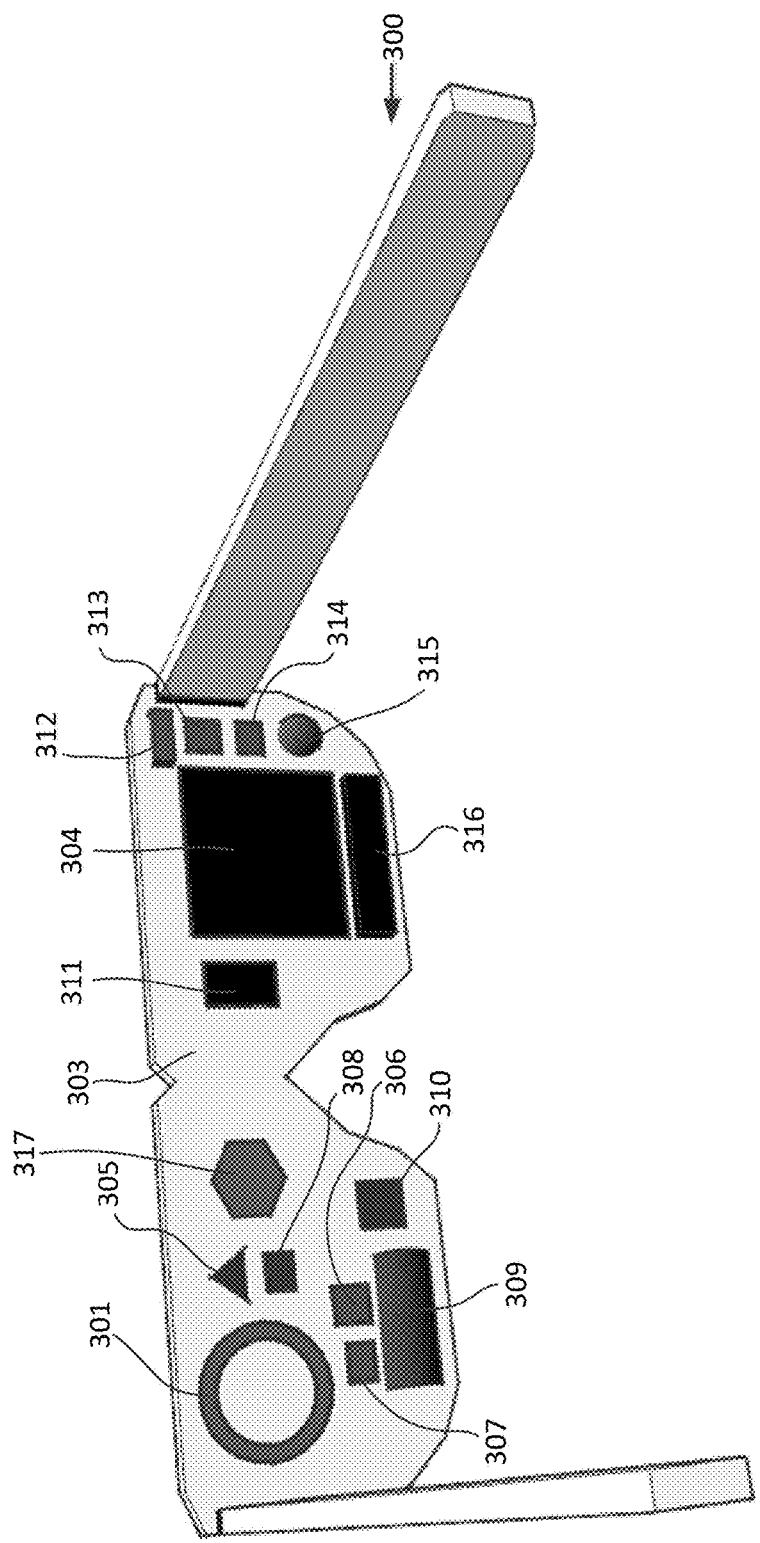
FIG. 6 shows a rear perspective view of an RFID data retrieval device according to the present invention.
Figure 7:
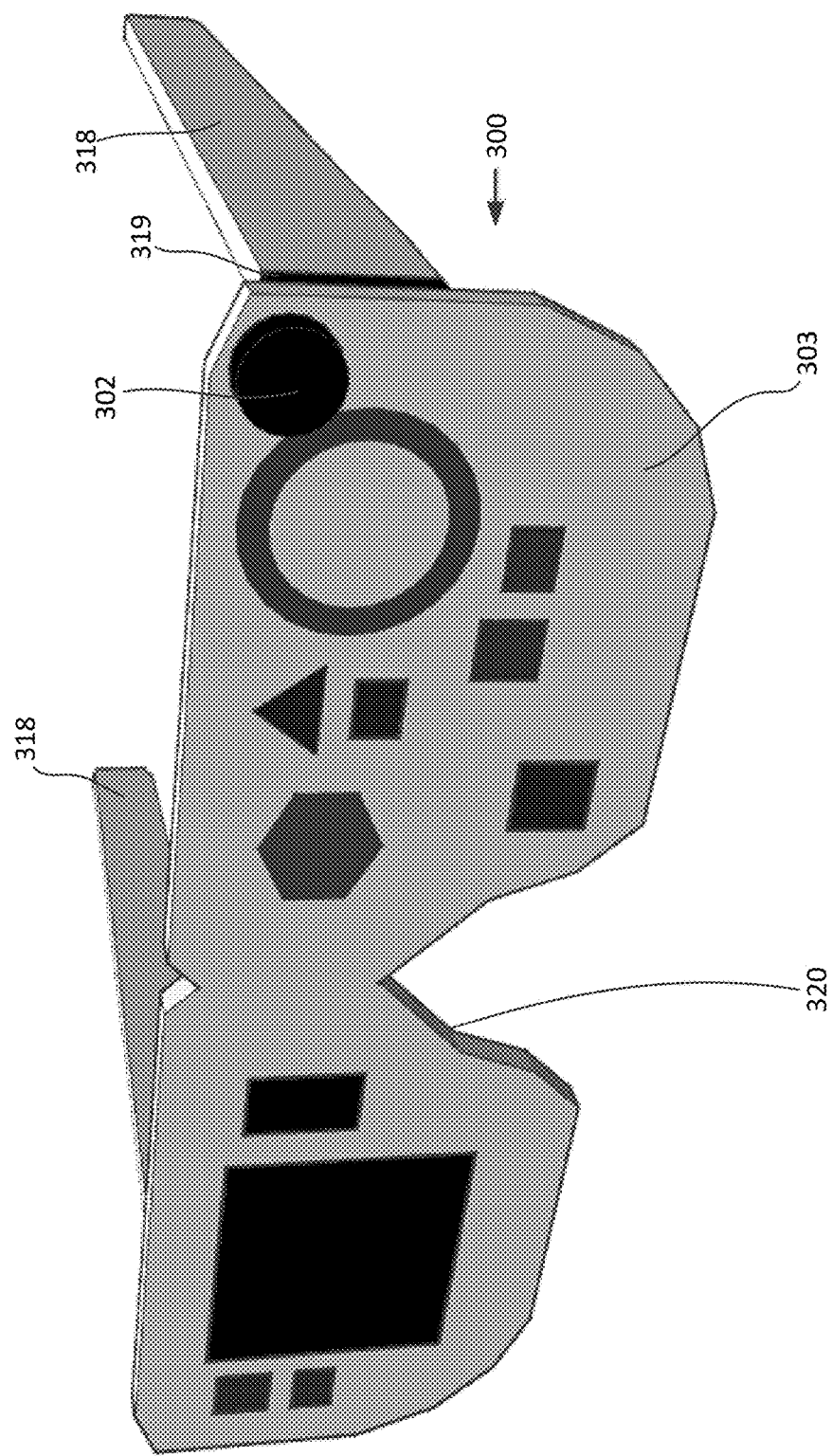
FIG. 7 shows a frontal perspective view of an RFID data retrieval device according to the present invention.

An example of this is depicted step-by-step in FIG. 5. Based on the contents of the first memory chip 202, the eyeglasses controller 304 depicted in FIG. 6 (a part of the eyeglasses data retrieval device 300) can generate an audio voice signal, which is sent to audio digital-to-analog converter (DAC) 313, then on to audio amplifier 314, and finally output to the user through audio speaker 315. FIG. 7 shows that these components are all attached to the device controller chip retaining member 303. This controller chip retaining member 303 contains a cutout for the user's nose 320, and is attached to a pair of opposing temporal side members 318 via a pair of hinges 319. The device controller chip retaining member cutout 320 allows the eyeglasses data retrieval device 300 to sit on the user's nose, and the temporal side members 318 secure the device 300 to the user's head above the ears.

The voice message output through speaker 315 can be the medicine name, dosage information, or usage instruction for the medicine. The second memory chip 311 on the glasses retrieval device 300 can be used to store a database of medicines or a medicine code library. Based on the medicine code that the eyeglasses device controller chip 304 reads from the first memory chip 202 attached to the RFID data label 200, the device controller chip 304 can search the database for the associated information, generate a voice message, and play it back to the user through speaker 315.

Additionally, an inertial measuring unit (IMU) 317 can be affixed to the eyeglasses retrieval device 300. This IMU 317 can provide the eyeglasses retrieval device 300 with motion and orientation information which can be interpreted as user input commands. For example, when the user nods or shakes his head, the device controller chip 304 can interpret the motion as "ENTER" or "EXIT" commands. The IMU 317 can also be used for tracking activity such as walking direction, number of footsteps, or whether the user is about to fall. These activity records can be stored in the second memory unit 311, and which can be replayed back to the user by voice.

The eyeglasses data retrieval device 300 also has a proximity sensor 302 attached to the device controller chip retaining member 303. This proximity sensor 302 can be optical, capacitive, or inductive, so long as it can measure a proper distance in front of the eyeglasses data retrieval device 300 (that is, so long as it can sense the proximity of an RFID label 200 at a programmed distance). The eyeglasses data retrieval device 300 may also include other sensors, such as ambient light and temperature sensors, which would help the user maintain awareness of his surrounding environment, or optical color sensors to help the user recognize the color of objects, thermal infrared cameras to help the user detect people or fire, and a heading source in the field of view of the camera. Additionally, the rear view of the eyeglasses data retrieval device 300, FIG. 6, shows that the device also contains an external interface 312, connected to device controller chip 304, which allows the device to connect to an external computer or network for data transfer. This external interface 312 can connect to an external computer or network via a wired connection (such as USB or Ethernet standards) or a wireless connection (such as the IEEE 802.11 standard, certified under the certification mark WI-FI® or under the BLUETOOTH® standard).

The eyeglasses data retrieval device 300 additionally contains a second loop antenna 301, which is used for two purposes. Firstly, the second loop antenna 301 connects to a switch 305, which connects the second loop antenna 301 to a wireless transceiver 308. This wireless transceiver 308 is connected to the device controller chip 304. Secondly, the switch 305 connects the second loop antenna 301 to an energy harvester 306. In normal operation mode, the device controller chip 304 configures the switch 305 to connect to the wireless transceiver 308 (and is disconnected from the energy harvester 306). In charging mode, the device controller chip 304 configures the switch 305 to disconnect the wireless transceiver 308 and connect the energy harvester 306 to the second loop antenna 301. Alternatively, the device may embody two loop antennas, one for receiving radio signals (processed through the wireless transceiver 308) and one connected to the energy harvester 306 for charging the device. In such a configuration, the switch 305 may be omitted.

Figure 8:
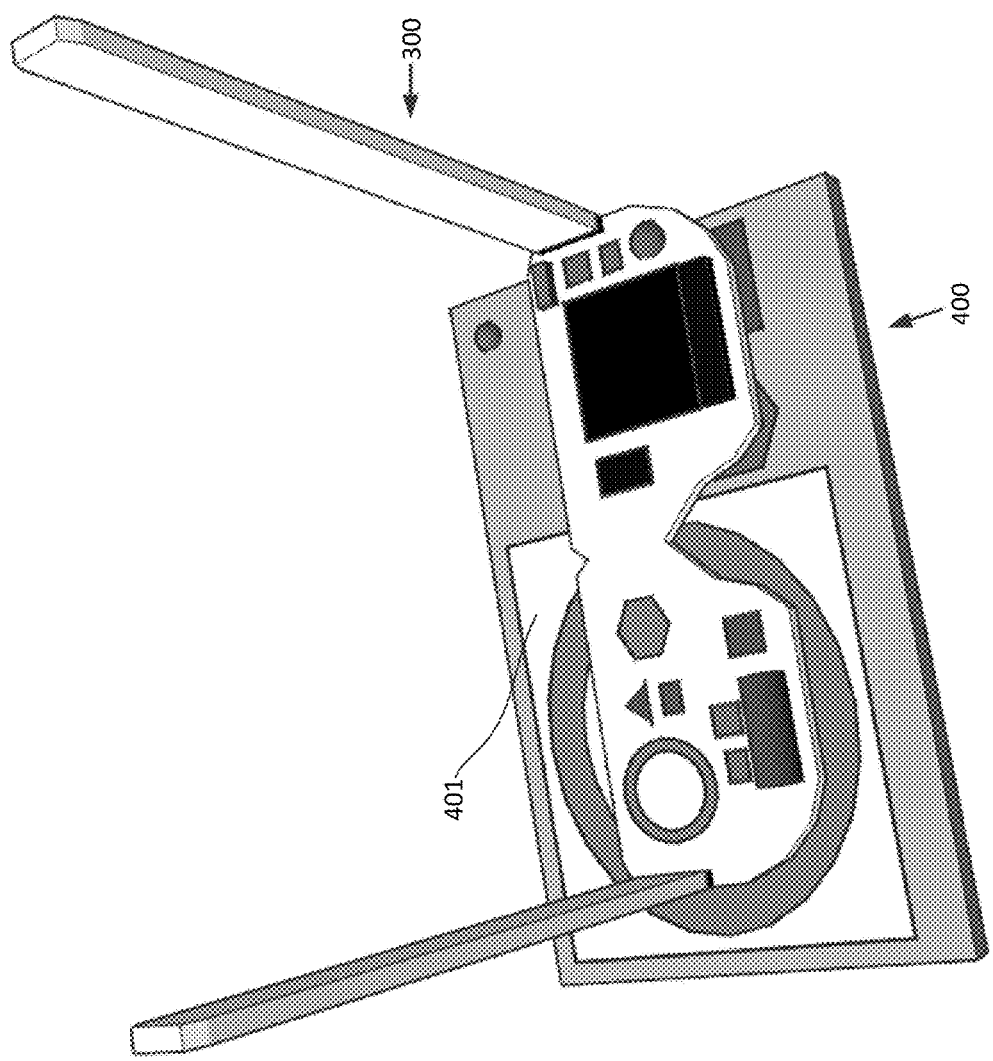
FIG. 8 shows the interaction between an RFID data retrieval device and an inductive charging device according to the present invention.
Figure 9:
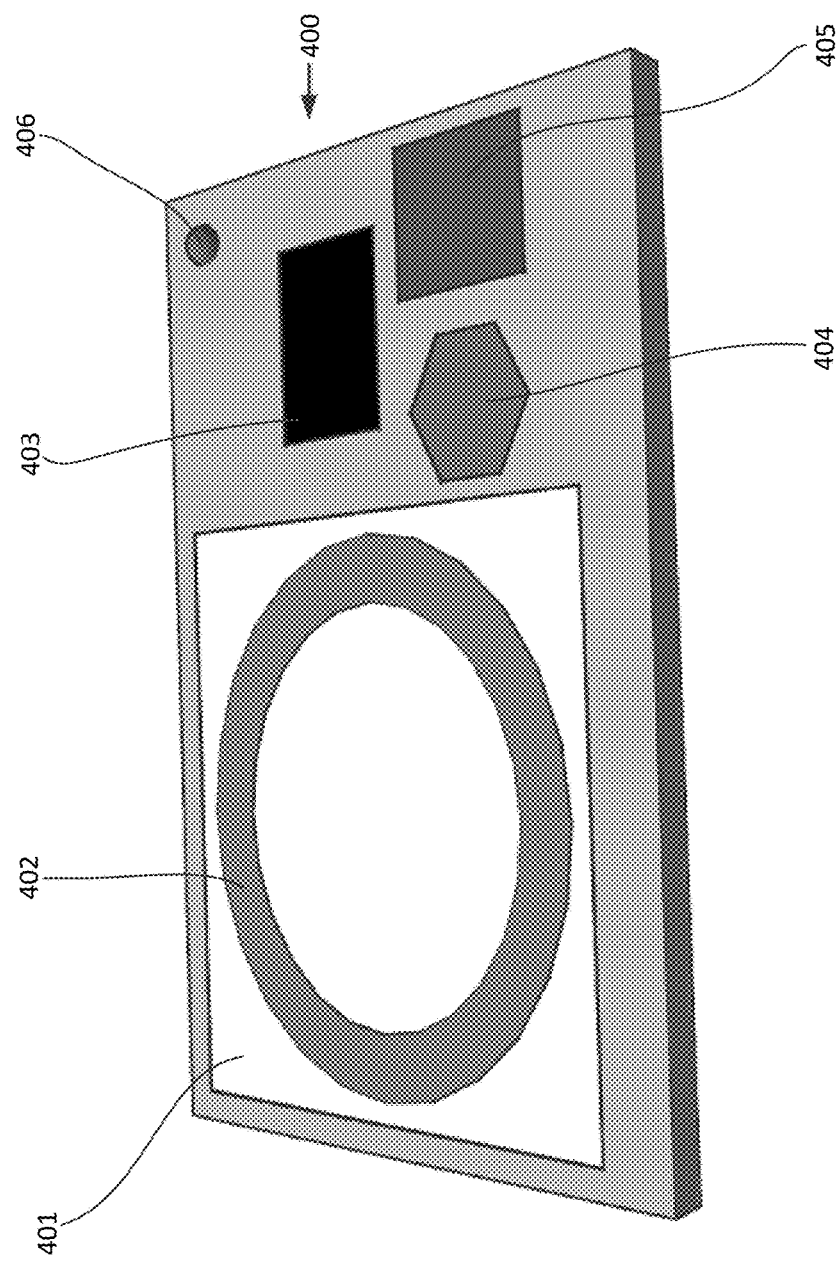
FIG. 9 shows a perspective view of an inductive charging device according to the present invention.

FIG. 8 illustrates the eyeglasses data retrieval device 300 as it is being charged. When the battery level on the device 300 is low, the user can place it on the charge region 401 of an inductive charging device 400 to charge the battery. FIG. 9 depicts the inductive charging device 400 in greater detail. The inductive charging device 400 contains an inductive charge coil 402 and an inductive charge region 401. The second loop antenna 301 on the eyeglasses data retrieval device 300 serves as a conductive loop on the eyeglasses data retrieval device 300. As soon as the second loop 301 is present in the charge region 401 of the inductive charging device 400, the charge controller 403 detects this presence through inductive charge coil 402 or charge region 401 and commands the regulator 405 and power converter 404 to begin the charge process through inductive charge coil 402. The inductive charging device 400 can indicate charge status via charging status indicator 406. This charging status indictor 406 can indicate with visual or audio messages when the charging is done. In alternative embodiments, a loop antenna may be constructed by making a conductive loop along the eyeglasses frame.

Figure 10:
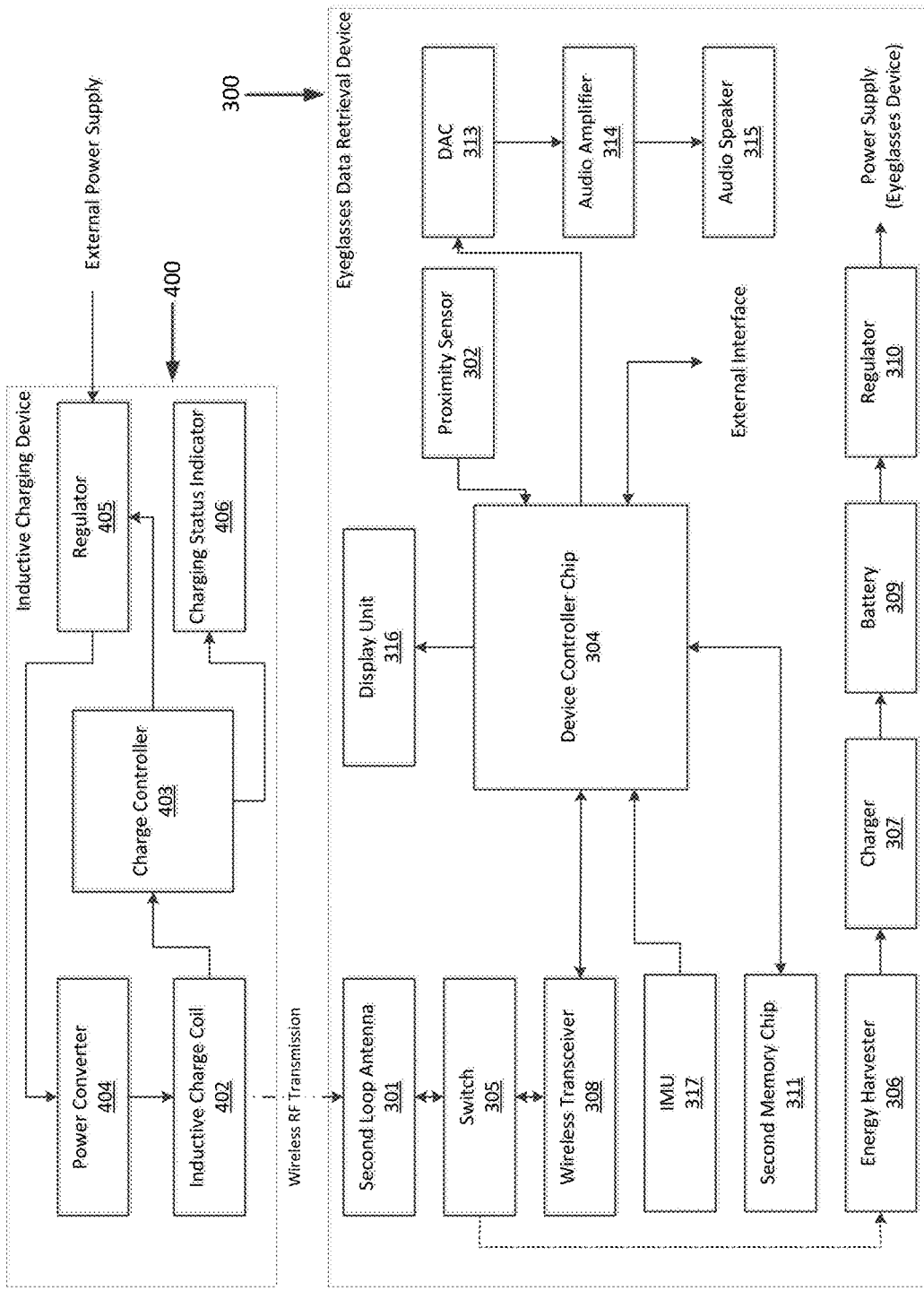
FIG. 10 shows a diagram of an embodiment of a system including an RFID data retrieval device and an inductive charging station according to the present invention.

FIG. 10 shows a block diagram of the components of the inductive charging device 400 and eyeglasses data retrieval device 300. When the eyeglasses data retrieval device 300 is in place in the charge region 401 on the inductive charging device 400, the charge controller 403 begins the charging process. The power converter 404 is commanded to convert DC voltage from an external power supply to RF energy. This RF energy is then emitted out through the inductive charge coil 402. This RF energy is then received by the second loop antenna 301 on the eyeglasses data retrieval device 300. When the wireless transceiver 308 detects the RF energy from the external source, it informs the device controller chip 304 to command the switch 305 to disconnect the second loop antenna 301 from the wireless transceiver and connect the loop antenna to the energy harvester 306. The RF energy from the inductive charge coil 402 thus goes to the energy harvester 306, where it is converted to DC voltage. The charger 307 connected to the energy harvester 306 and battery 309 manages the charging process, using energy gathered by the energy harvester 306 to fill the battery 309. The charger 307 can also inform the device controller chip 304 of the charging status, allowing the device controller chip 304 to be aware of the time of charge and level of charge. The device controller chip 304 can relay this information to the user via display unit 316 or through audio speaker 315.

Figure 11:
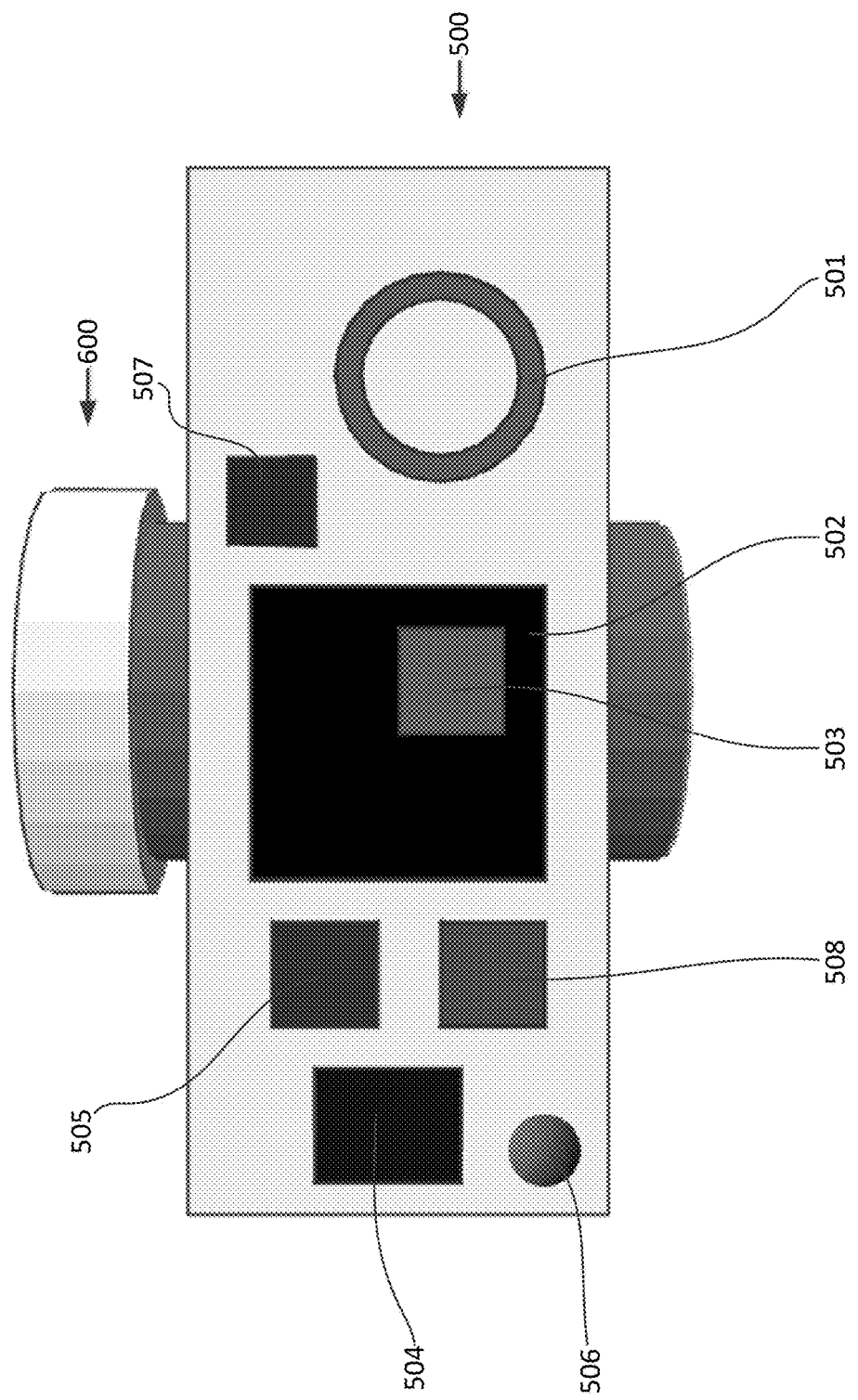
FIG. 11 shows a frontal elevation view of an RFID label with a wireless and wired memory chip according to the present invention.
Figure 12:
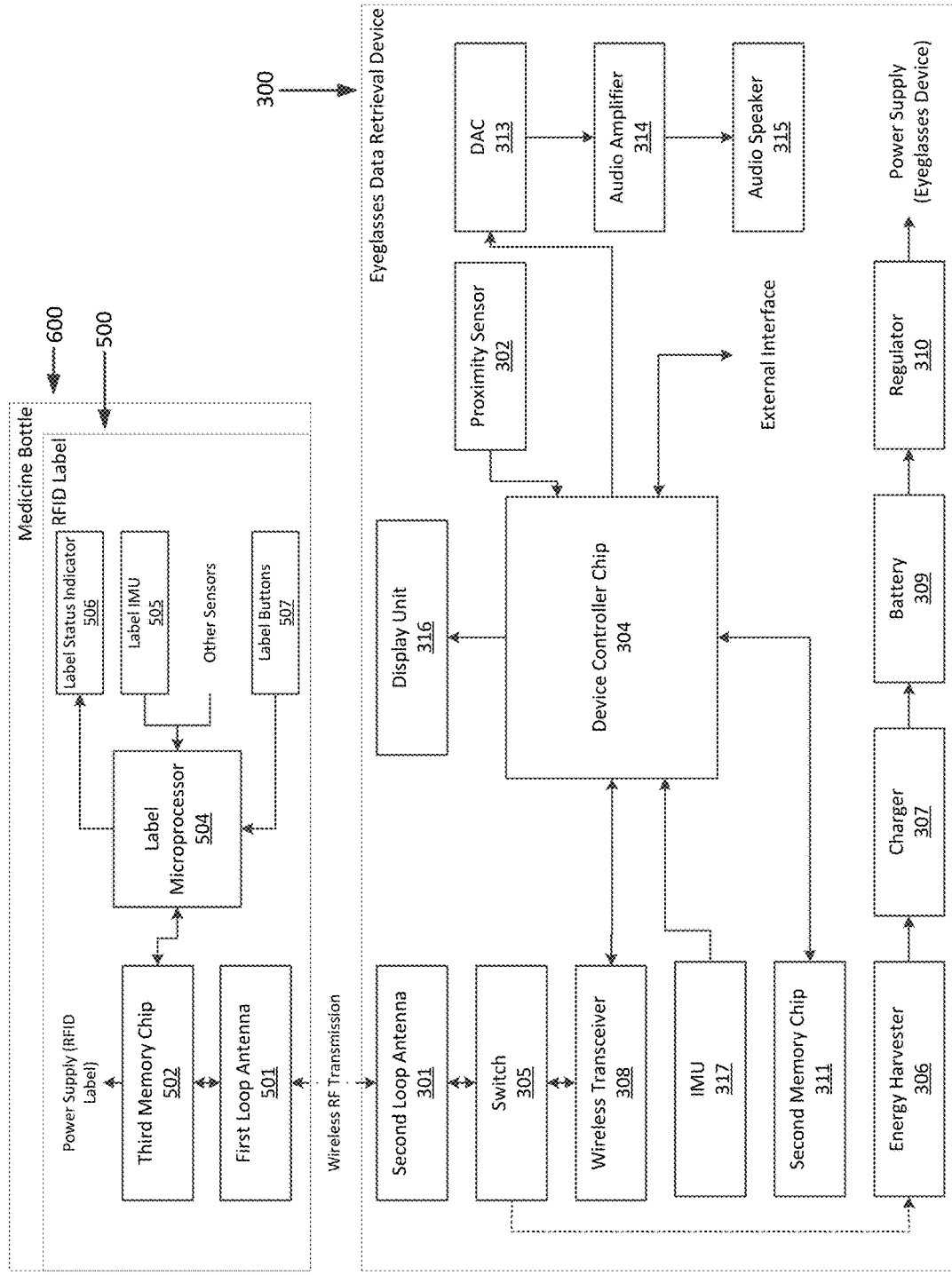
FIG. 12 shows a diagram of an embodiment of a system including an RFID data retrieval device and an RFID label with a wireless and wired memory chip according to the present invention.

FIG. 11 depicts another embodiment of the RFID data label 500, with the wireless only first memory chip 202 replaced by a third memory chip 502 capable of being accessed through both wired and wireless means. The embodiment in FIG. 11 has the addition of a label microcontroller 504, label IMU 505, label hard wire interface 508, label button interface 507, and label status indicator 506. Whereas the wireless only configuration of the RFID label 200 depicted in FIGS. 4 and 5 means that the first memory chip 202 could only be accessed via wireless signal, the additional configuration in FIG. 12 replaces the first memory chip 202 with a third memory chip 502, configured to be accessed both through a label hard wire interface 508 (e.g., via USB or other data port) and wirelessly via the first loop antenna 501. Additionally, the label microcontroller 504 is configured to write data to the third memory chip 502. Hence, in this configuration, the user can write data via wireless interface to the third memory chip 502 by using the eyeglasses data retrieval device 300 (where the device controller chip 304 is configured to send data out via second loop antenna 301), or via the label hard wire interface 508. FIG. 12 illustrates the additional embodiment of the RFID label 500 shown in detailed block diagram format.

Figure 13:
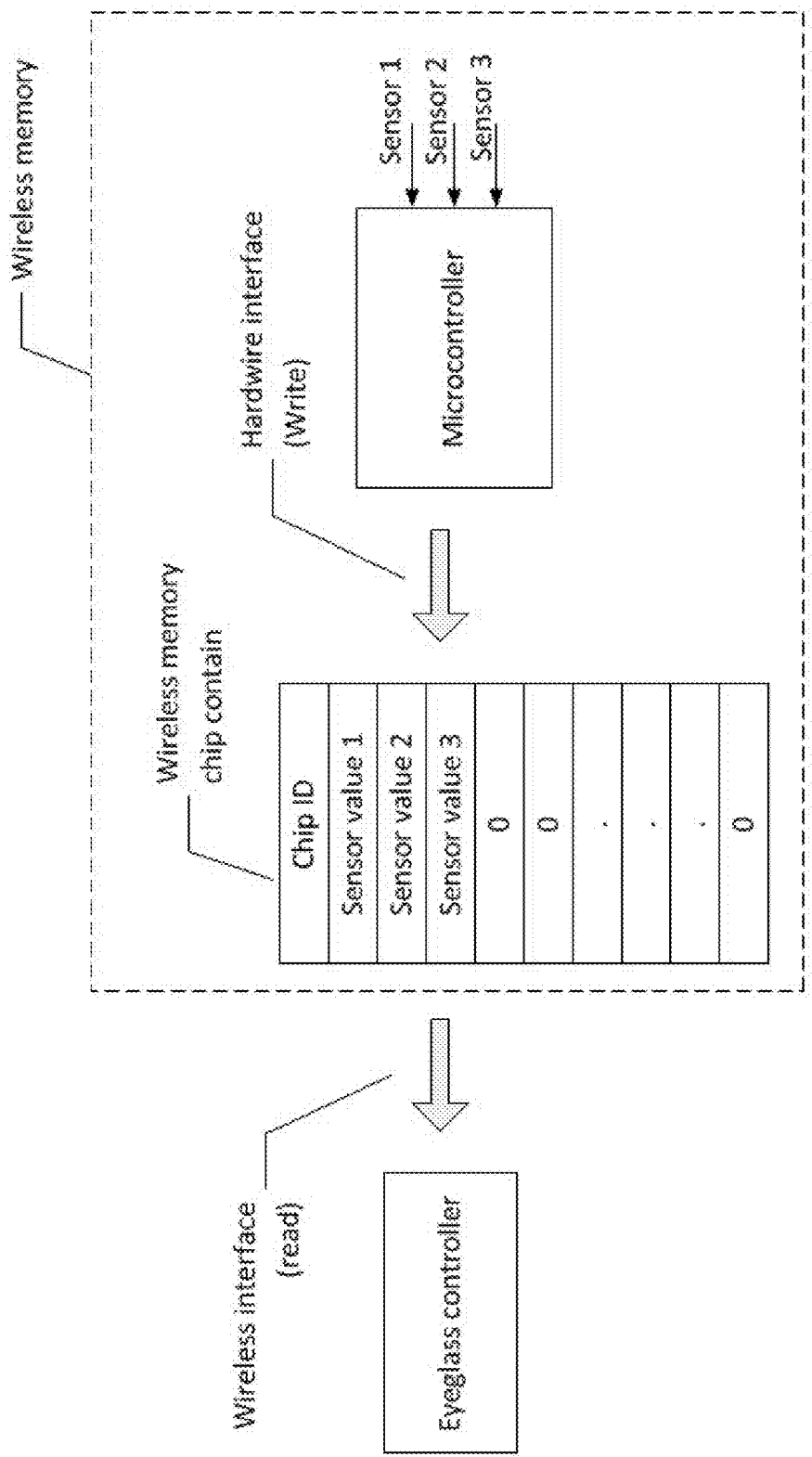
FIG. 13 shows a diagram depicting read and write from and to a wireless or wired memory chip on an RFID label according to the present invention.

FIG. 13 illustrates the read and write activity from the third memory chip 502 both via the label hard wire interface 508 and wirelessly via the first loop antenna 501. As with the first memory chip 202 of the first embodiment of the RFID label 200 shown in FIG. 4, the third memory chip 502 of the second embodiment shown in FIG. 11 has an internal energy harvesting circuit 503 which converts RF energy 102 received from the eyeglasses device controller 304 to energy (a voltage source). This voltage source supplies power for the label microcontroller 504, label status indicator 506, label IMU 505, label button 507, and other sensors on the RFID label 500. The label IMU 505 can provide orientation information of the RFID label 500 (and because it is attached to medicine bottle 600, orientation information for the medicine bottle 600 itself). This orientation information can be output to the data retrieval device 300 device microcontroller chip 304. In such a configuration, each orientation of the RFID label 500 can represent an input message for the device microcontroller chip 304. For example, when the user rotates the medicine bottle 600 along the Z-axis (the long axis), the eyeglasses data retrieval device 300 can inform the user of a different bit of information about the medicine. Additional sensors for this embodiment might include color sensors capable of detecting the color of medicine, image sensors that can recognize the shape of pills and any text codes printed on the pills. Using this information, the colors, shapes, and text codes of medicines can be compared against a database to verify the correct medicine is in the correct medicine bottle 600. Additionally, the label microcontroller 504 may be configured to transmit a special signal to the data retrieval device 300 when the label button 507 is pressed (such as a call for help, or an alarm call).

Figure 14:
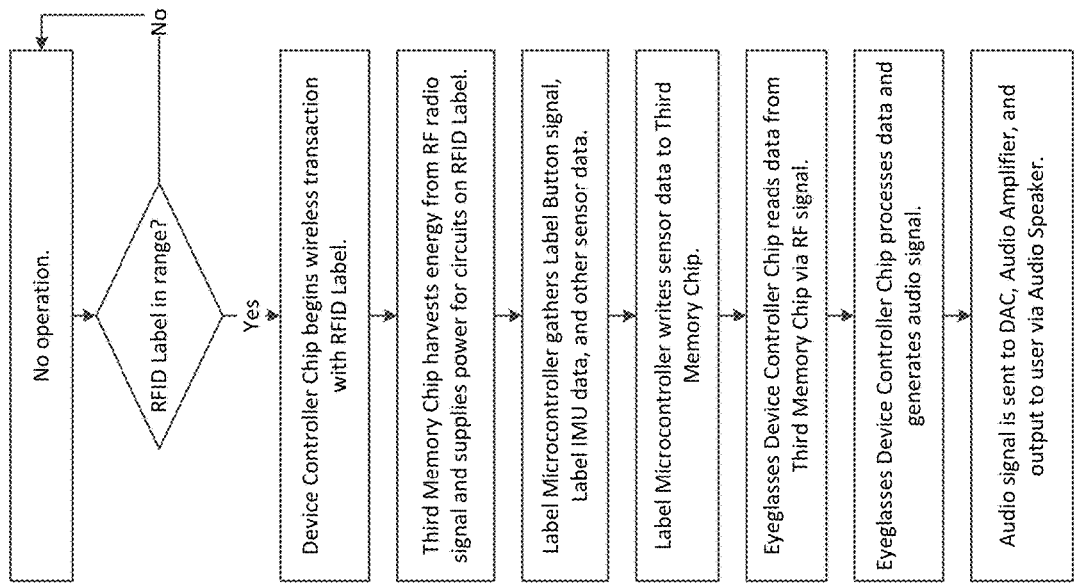
FIG. 14 shows a diagram depicting a process according to which an RFID data retrieval device accesses data on an RFID label according to the present invention.

FIG. 14 illustrates the steps for the embodiment of RFID label 500 to write label IMU 505 (or other sensor) data to the third memory chip 502, and for the eyeglasses data retrieval device 300 to access this information and output it to the user. When the proximity sensor 302 on the eyeglasses data retrieval device 300 detects that the RFID label 500 is within range, the device controller chip 304 will initiate the wireless transaction with the RFID label 500 by sending out an RF signal via the second loop antenna 301. On the RFID label 500, the first loop antenna 501 receives the radio signal, and the energy harvesting circuit 503 harvests the energy from the RF signal to supply power to the electronic components on the RFID label 500. Using this power, the label microcontroller 504 gathers the signal from the label button 507, label IMU 505 sensor data, and any data from other sensors present on the RFID label 500 and writes this information to the third memory chip 502. The label microcontroller 504 then sends this data along with data about the medicine contained on the third memory chip 502 out to the data retrieval device 300 through first loop antenna 501, to be received by second loop antenna 301. The eyeglasses device controller chip 304 then reads and processes this data, and generates and outputs an audio message to the user through the DAC 313, audio amplifier 314, and audio speaker 315 or a visual message via display unit 316.

Many modifications and variations of the system for Multifunctional Wearable Object Identified Glasses for the Visually Handicapped are possible in light of the above description. Within the scope of the appended claims, the embodiments of the systems described herein may be practiced otherwise than as specifically described. The scope of the claims is not limited to the implementations and the embodiments disclosed herein, but extends to other implementations and embodiments as may be contemplated by those having ordinary skill in the art.

I claim:

1. A system comprising:
   a radio frequency identification label comprising a first memory chip electrically connected to a first loop antenna and an energy harvesting circuit electrically connected to the first memory chip, said first memory chip containing information relating to a medicine being taken by a visually impaired person; and
   a retrieval device comprising
      a device controller chip;
      a wireless transceiver electrically connected to said device controller chip, a switch electrically connected to the wireless transceiver, and a second loop antenna electrically connected to the switch;
      a second memory chip electrically connected to the device controller chip;
      a proximity sensor electrically connected to the device controller chip;
      an audio digital-to-analog converter connected to said device controller chip, an audio amplifier connected to the digital-to-analog converter, and an audio speaker connected to the audio amplifier; and a pair of opposing temporal side members, each hingedly mounted to a device controller chip retaining member, said device controller retaining member having a recess for a nose of the visually impaired person, and the device controller chip connected to the device controller chip retaining member;

wherein the device controller chip is configured to command the wireless transceiver to transmit frequency (RF) energy from the second loop antenna to the first loop antenna when the proximity sensor detects the radio frequency identification label.

2. The system of claim 1, wherein the retrieval device further comprises: an inertial measuring unit connected to the device controller chip.

3. The system of claim 1, wherein the retrieval device further comprises: a display unit connected to the device controller chip.

4. The system of claim 1, wherein the retrieval device further comprises: an external interface unit connected to the device controller chip.

5. The system of claim 1, wherein the retrieval device further comprises: an energy harvester connected to the switch, a charger connected to the energy harvester, a battery connected to the charger, and a regulator connected to the battery.

6. The system of claim 1, further comprising:
an inductive charging device comprising
an inductive charge coil connected to a charge region, a power converter connected to the inductive charge coil, a regulator connected to the power converter, a charge controller connected to the power converter, and a charging status indicator connected to the charge controller;
wherein the charge controller is configured to command the power converter to convert direct current (DC) received via the regulator to RF energy and emit RF energy via the inductive charge coil when the retrieval device touches the charge region, wherein the device controller chip is configured to command the switch to disconnect the second loop antenna from the wireless transceiver and connect the second loop antenna to the energy harvester when the wireless transceiver receives RF energy from the second loop antenna.

7. A system comprising:
a radio frequency identification label comprising
a first memory electrically connected to a first loop antenna and an energy harvesting circuit electrically connected to the first memory, said first memory containing information relating to a medicine being taken by a visually impaired person;
a label IMU connected to a label microcontroller, a label button connected to the label microcontroller, a label status indicator connected to the label microcontroller, a label hard wire interface connected to the label microcontroller, said label microcontroller connected to the first memory; and a retrieval device comprising
a device controller chip;
a wireless transceiver electrically connected to said device controller chip, a switch electrically connected to the wireless transceiver, and a second loop antenna electrically connected to the switch;
a second memory chip electrically connected to the device controller chip;
a proximity sensor electrically connected to the device controller chip;
an audio digital-to-analog converter connected to said device controller chip, an audio amplifier connected to the digital-to-analog converter, and an audio speaker connected to the audio amplifier; and
a pair of opposing temporal side members, each hingedly mounted to a device controller chip retaining member, said device controller retaining member having a recess for a nose of the visually impaired person, and the device controller chip connected to the device controller chip retaining member;
wherein the device controller chip is configured to command the wireless transceiver to transmit frequency (RF) energy from the second loop antenna to the first loop antenna when the proximity sensor detects the radio frequency identification label.

8. The system of claim 7, wherein the retrieval device further comprises: an inertial measuring unit connected to the device controller chip.

9. The system of claim 7, wherein the retrieval device further comprises: a display unit connected to the device controller chip.

10. The system of claim 7, wherein the retrieval device further comprises: an external interface unit connected to the device controller chip.

11. The system of claim 7, wherein the retrieval device further comprises: an energy harvester connected to the switch, a charger connected to the energy harvester, a battery connected to the charger, and a regulator connected to the battery.

12. The system of claim 7, further comprising:
an inductive charging device comprising
an inductive charge coil connected to a charge region, a power converter connected to the inductive charge coil, a regulator connected to the power converter, a charge controller connected to the power converter, and a charging status indicator connected to the charge controller;
wherein the charge controller is configured to command the power converter to convert direct current (DC) received via the regulator to RF energy and emit RF energy via the inductive charge coil when the retrieval device touches the charge region, wherein the device controller chip is configured to command the switch to disconnect the second loop antenna from the wireless transceiver and connect the second loop antenna to the energy harvester when the wireless transceiver receives RF energy from the second loop antenna.

* * * * *